United States Patent [19]

Thornton

[11] 4,142,538

[45] Mar. 6, 1979

[54] DIFFERENT STIFFNESS CONTINUOUS LENGTH TEETH CLEANER

[76] Inventor: Thomas F. Thornton, 221 Mill Rd., New Canaan, Conn. 06840

[21] Appl. No.: 760,194

[22] Filed: Jan. 17, 1977

[51] Int. Cl.² ............................................. A61C 15/00
[52] U.S. Cl. .................................................. 132/89
[58] Field of Search ...................... 132/89, 91, 93, 89

[56] References Cited

U.S. PATENT DOCUMENTS

| | | | |
|---|---|---|---|
| 1,069,874 | 8/1913 | Hanscom | 132/89 |
| 2,612,177 | 9/1952 | Footer | 132/93 |
| 3,153,418 | 10/1964 | Fleming | 132/93 |
| 3,511,249 | 5/1970 | Baitz | 132/89 |
| 3,789,858 | 2/1974 | Pesce | 132/89 |
| 3,830,246 | 8/1974 | Gillings | 132/89 |
| 3,837,351 | 9/1974 | Thornton | 132/89 |
| 3,838,702 | 10/1974 | Standish | 132/89 |
| 3,896,824 | 7/1975 | Thornton | 132/89 |
| 3,930,059 | 12/1975 | Wells | 132/91 |
| 3,942,539 | 3/1976 | Corliss | 132/91 |
| 4,008,727 | 2/1977 | Thornton | 132/89 |

FOREIGN PATENT DOCUMENTS 1008368  12/1975  Canada ...................................... 132/89

*Primary Examiner*—G.E. McNeill
*Attorney, Agent, or Firm*—Ernest M. Junkins

[57] ABSTRACT

A continuous length of interproximal space tooth cleaner consisting of textured yarn that is composed of deformed filaments throughout its complete length with a hardened covering being applied on selected extents thereof without applying an elongating force to the extents.

6 Claims, 3 Drawing Figures

DIFFERENT STIFFNESS CONTINUOUS LENGTH TEETH CLEANER

The present invention constitutes an improvement in the continuous length tooth cleaner disclosed and claimed in my U.S. Pat. No. 3,837,351, granted Sept. 24, 1974, and entitled "Interdental Tooth Cleaner and Method of Making Same". The tooth cleaner disclosed in said patent consists of a continuous length of textured yarn formed by a plurality of deformed filaments. The yarn is coated throughout its length with a hardened covering which renders it effective to clean teeth.

While such a tooth cleaner has been found to be satisfactory, the use of a single covering caused the yarn to have the same characteristics of stiffness, abrasiveness, etc., throughout its length. One desired characteristic of a tooth cleaner is to have the yarn filaments capable of being easily straightened to become parallel and separable and act as a string when it is desired to insert the cleaner through close crowns into an interproximal space. Another characteristic desired is to have the yarn remain bulky for substantially filling the interproximal space when the cleaner is in and being pulled through the space and thus act as a brush. The cleaner disclosed in my above-noted patent by having constant characteristics was incapable of completely meeting both requirements and thus, the effect of the hardened covering on the yarn was the result of a compromise between a desired relatively stiff brush and a desired relatively easily straightened string.

It is accordingly an object of the present invention to provide a continuous length cleaner which has extents which more completely satisfy the unique requirements of a brush and a string with the extents alternating along the continuous length.

Another object of the present invention is to achieve the above object with a continuous length cleaner which is constructed and arranged to enable the user to readily perceive which extents have brush characteristics and which have string characteristics.

A further object of the present invention is to achieve the above objects with a continuous length cleaner for interproximal spaces between teeth which may be easily and economically manufactured by the method of the present invention.

Still another object of the present invention is to provide a continuous length tooth cleaner which has extents of different stiffness.

In the continuous length tooth cleaner of the present invention, a continuous length of textured yarn is preferably initially processed into a tooth cleaner to provide a cleaner constructed essentially as disclosed in my above-noted patent. There is thus a hardened covering extending throughout the length of the cleaner with the covering being that which produces the characteristics most desired by a string. After this covering has hardened, the present invention adds a second covering to the length but only on selected extents of the yarn where it is desired to have those characteristics of a brush. The second covering is applied as a liquid and hardened with the filaments in a relaxed condition, i.e., deformed, rather than when they are in a tensioned, straight condition as occurs when the first covering is applied. The filaments of the second covering extents of the cleaner have a much greater resistance to being straightened than the one covering portions which imparts a greater stiffness and abrasiveness to the brush extents as compared to the string extents.

It has, moreover, been found desirable to make the second covering have a different color than the first covering so that the user may be able to easily perceive the characteristics of each extent of the cleaner to thus choose those extents which are presently desired.

Other features and advantages will hereinafter appear:

In the drawing.

Figure 1:
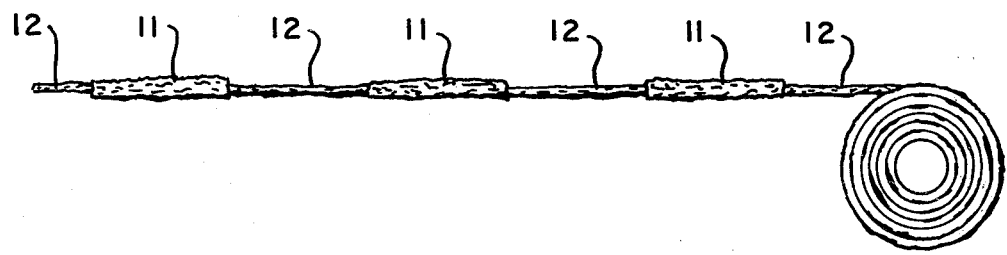
FIG. 1 is a view of a length of tooth cleaner of the present invention having extents of different stiffness.
Figure 2:
FIG. 2 is an enlarged view of a portion of the cleaner.

Referring to the drawing, a continuous length of tooth cleaner is generally indicated by the reference numeral 10 and includes brush extents 11 that alternate along the length of the cleaner 10 with string extents 12. As disclosed in my above-noted patent, a continuous length of textured yarn is initially stretched to cause its deformed filaments to become essentially parallel. A liquid covering, such as nylon suspended in alcohol, is applied and the covering is allowed to dry and harden with the final hardening occurring without any substantial tension on the filaments. The filaments thus revert to their essentially initial condition wherein the filaments are deformed.

Figure 3:
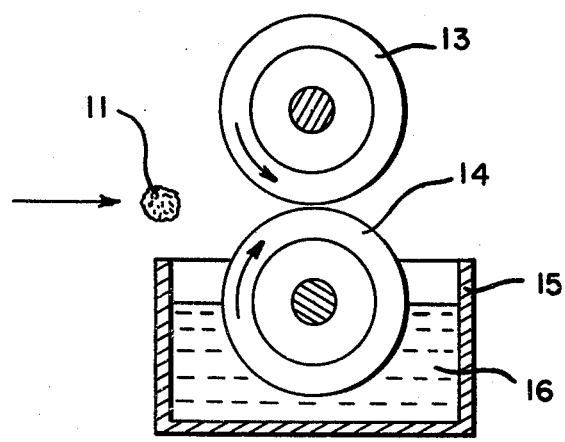
FIG. 3 is a diagrammatic representation of an apparatus and method for applying the second covering.

In accordance with the present invention, a second covering of hardenable material, which again may be nylon suspended in alcohol, is applied to the single covering cleaner but only at those extents where it is desired to have the brush extents 11. As diagrammatically shown in FIG. 3, one manner of applying the second covering is to use a covering apparatus that includes two rollers 13 and 14 mounted coaxially for rotation in the direction shown by their respective arrows. The lower roller 14 is partially submerged in a tank 15 having a liquid solution 16 of nylon suspended in alcohol. In use, an extent of the length is perpendicularly moved between the two rollers with the periphery of the rollers applying a covering of the solution 16. It will be noted that during the applying of the second covering there is no elongation force applied to the continuous length so that the filaments are in their deformed state when they are coated. The coating is hardened also without any tension being applied on the extent. The rollers tend to squeeze the brush extent filaments so that the cross-sectional area of the brush extents is not increased and generally is decreased to be lesser than the area of the string extents. The diameter of the brush extents 11 in the drawing are exaggerated for clarity.

Preferably, the length of the rollers approximates the extent of the brush extents 11 so that only one pass through the rollers is sufficient to provide the desired length of the extent.

As an indication of the different stiffness characteristics imparted in the continuous cleaner by the present invention, Applicant has found that if a 600 denier yarn of high tenacity nylon filaments before being covered requires a pull of 8–16 ozs. to essentially remove the deformation of the filaments and cause them to become straight and parallel, the application of the single covering surprisingly decreases the elongating force necessary to effect removal of the deformation. If the yarn above-noted is covered as disclosed in my above-noted patent, only an elongating force on the order of perhaps 4–6 ozs. is required to straighten the filaments. On the other hand, a length of yarn having the two coverings applied as herein disclosed, requires a pull of substantially 2 pounds before the filaments even begin to elongate and moreover, there is a tendency to approach the breaking strength of the filaments, which may be on the order of 7 pounds, prior to complete removal of the deformation. Thus, the present invention provides a continuous length of yarn having two alternating extents, one formed with a single covering and the other formed with a double covering so that the extents have a relative stiffness on the order of five or more to one.

Such a high stiffness ratio assures that the user will be able to easily effect straightening of the string extents without destroying the bulkiness of the brush extents and hence its brush capabilities. The second covering on the brush extents has also been found to increase the abrasiveness of the brush extents and hence its effectiveness for dental hygiene.

While the one covering string extents actually require a lesser elongating force to remove the deformation of the filaments than the original, uncovered yarn, the difference is not so large as to vary the large ratio between the brush and string stiffness. Thus, it is also contemplated that the string extents may not be provided with a covering and that only the second covering be applied.

It will accordingly be understood that there has been disclosed a continuous length of interproximal space tooth cleaner having alternate string and brush extents. As desired, the string extents require only a slight elongating force to cause the filaments to become straight and parallel while, also as desired, the filaments of the brush extents will remain deformed even when the elongating force is multiplied many times. The difference in stiffness is produced by the applying of a hardened covering on just the brush extents without exerting an elongating force on said extents.

Variations and modifications may be made within the scope of the claims and portions of the improvements may be used without others.

I claim:

1. An interproximal tooth cleaner comprising a length of continuously textured yarn formed of a plurality of filaments that have been individually permanently deformed and crinkled throughout the length of the cleaner and means subdividing the length into brush extents and string extents with the extents alternating along the length and with the brush extents having a substantially greater stiffness than the string extents, said means including a hardened covering applied only on the filaments of the brush extents, the permanently deformed and crinkled filaments forming both brush and string extents being capable of being straightened by an elongating force and in which the brush extents have a resistance to the straightening of their filaments by at least five times the resistance of the string extent filaments.

2. The invention as defined in claim 1 in which there is an initial hardened covering applied throughout the continuous length and in which the first-mentioned hardened covering is applied over the initial covering.

3. The invention as defined in claim 2 in which the initial hardened covering is applied as a liquid when the filaments are essentially straight and parallel and in which the first-mentioned covering is applied as a liquid when the filaments are in their deformed state.

4. The invention as defined in claim 2 in which the initial hardened covering reduces the resistance of the filaments in the string extents to being straightened to less than the resistance of the yarn prior to the initial covering being applied thereto.

5. The invention as defined in claim 2 in which the initial hardened covering has one color and the first-mentioned covering a readily perceivable different color.

6. The method of providing a continuous length of an interproximal space tooth cleaner having alternating brush extents and string extents with the brush and string extents being formed of permanently deformed and crinkled filaments which are capable of being straightened by the application of an elongating force comprising the steps of supplying a continuous length of textured yarn formed of a plurality of individually deformed and crinkled filaments and forming a hardened covering on the brush extents by hardening a liquid applied to the brush extents while the filaments thereof are crinkled and deformed by the absence of an elongating force on said brush extent filaments, in which there is the step of forming an initial covering on the complete length of yarn with the initial covering being applied as a liquid while an elongating force is being applied to the yarn to cause the filaments to be essentially straight and parallel and in which the step of forming the hardened covering is performed after the step of forming the initial covering.

* * * * *